United States Patent
Bruder et al.

(10) Patent No.: US 6,916,899 B2
(45) Date of Patent: Jul. 12, 2005

(54) POLYCARBONATES, POLYESTER CARBONATES AND POLYESTERS HAVING LATERAL, CYCLOALKYL-SUBSTITUTED PHENOLS

(75) Inventors: Friedrich-Karl Bruder, Krefeld (DE); Helmut-Werner Heuer, Krefeld (DE); Alexander Meyer, Krefeld (DE); Rolf Wehrmann, Krefeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/772,785

(22) Filed: Feb. 5, 2004

(65) Prior Publication Data

US 2004/0158025 A1 Aug. 12, 2004

Related U.S. Application Data

(63) Continuation-in-part of application No. 10/687,862, filed on Oct. 17, 2003.

(30) Foreign Application Priority Data

Oct. 21, 2002 (DE) .......................... 102 48 952

(51) Int. Cl.$^7$ .............................. C08G 64/00
(52) U.S. Cl. ............... 528/196; 264/176.1; 264/219; 528/198; 528/271; 528/272
(58) Field of Search .............. 264/176.1, 219; 528/196, 198, 271, 272

(56) References Cited

U.S. PATENT DOCUMENTS

| | | | |
|---|---|---|---|
| 3,085,992 A | 4/1963 | Lee et al. .................. 260/47 |
| 3,166,606 A | 1/1965 | Reinking et al. ........... 260/860 |
| 3,173,891 A | 3/1965 | Fry et al. .................. 260/47 |
| 4,269,964 A | 5/1981 | Freitag et al. ............. 528/126 |
| 4,330,663 A | 5/1982 | Rosenquist ................ 528/176 |
| 4,624,802 A | 11/1986 | Schaper et al. ......... 252/522 R |
| 4,699,971 A | 10/1987 | Mark, deceased et al. .. 528/198 |
| 4,788,276 A | 11/1988 | Mark, deceased et al. .. 528/179 |
| 4,929,709 A | 5/1990 | Dujardin et al. ........... 528/198 |
| 5,043,403 A | 8/1991 | Dujardin et al. ........... 525/462 |
| 5,783,653 A | 7/1998 | Okamoto .................... 528/196 |
| 5,959,065 A | 9/1999 | Heuschen et al. .......... 528/198 |
| 6,140,475 A | 10/2000 | Margolin et al. ........... 528/196 |
| 6,252,036 B1 | 6/2001 | Hatono et al. ............. 528/274 |
| 6,258,922 B1 | 7/2001 | Okamoto et al. ........... 528/196 |
| 6,410,777 B1 | 6/2002 | Kaneko et al. .............. 560/68 |
| 6,596,840 B1 | 7/2003 | Kratschmer et al. ........ 528/196 |
| 2004/0049030 A1 * | 3/2004 | Bohm et al. ................ 540/596 |
| 2004/0059068 A1 * | 3/2004 | Nodera ....................... 525/474 |

FOREIGN PATENT DOCUMENTS

| | | |
|---|---|---|
| CA | 1331669 | 8/1994 |
| GB | 1 291 411 | 10/1972 |
| JP | 57-133149 | 8/1982 |
| JP | 63-215714 | 9/1988 |
| JP | 6-266499 | 9/1994 |
| JP | 2000-63508 | 2/2000 |
| WO | 98/22522 | 5/1998 |

OTHER PUBLICATIONS

Kunststoff–Handbuch, 3, L Bottenbruch, Hanser, Munich (month unavailable) 1992, pp. 127–129, "3.2 Chemischer Aufbau" Polycarbonate.

* cited by examiner

Primary Examiner—Terressa Boykin
(74) Attorney, Agent, or Firm—Joseph C. Gil; Aron Preis

(57) ABSTRACT

A process of using of a particularly substituted phenol as a chain terminator of a polymeric resin is disclosed. The chain terminator is a member selected from among ortho-substituted phenol, metha-substituted phenol, and their corresponding coupled esters. The polymeric resin is selected among polycarbonate, polyester carbonate and polyester. The thus chain terminated resin is suitable for producing molded parts and extrudates. Also disclosed are the process for producing these polymers and processes for producing the molded parts and extrudates.

21 Claims, No Drawings

POLYCARBONATES, POLYESTER CARBONATES AND POLYESTERS HAVING LATERAL, CYCLOALKYL-SUBSTITUTED PHENOLS

This application is a Continuation-In-Part of U.S. Ser. No. 10/687,862, filed Oct. 17, 2003.

FIELD OF THE INVENTION

The present invention concerns the use of phenolic compounds having o- and/or m-substituents as chain terminators in polycarbonates, polyester carbonates and polyesters, and polycarbonates, polyester carbonates and polyesters having terminal groups derived from o- and/or m-substituted phenols, molded parts and extrudates produced from these polymers, process for producing the polymers and process for producing the molded parts and extrudates.

SUMMARY OF THE INVENTION

A process of using of a particularly substituted phenol as a chain terminator of a polymeric resin is disclosed. The chain terminator is a member selected from among ortho-substituted phenol, metha-substituted phenol, and their corresponding coupled esters. The polymeric resin is selected among polycarbonate, polyester carbonate and polyester. The thus chain terminated resin is suitable for producing molded parts and extrudates. Also disclosed are the process for producing these polymers and processes for producing the molded parts and extrudates.

BACKGROUND OF THE INVENTION

Monofunctional phenol-based compounds such as e.g. phenol, 4-alkyl phenols and 4-cumyl phenol are frequently used as chain terminators in the production of polycarbonates (Kunststoff-Handbuch 3; L. Bottenbruch, Hanser, Munich 1992, p. 127; EP-A 0 353 594).

Polycarbonates having terminal groups derived from cycloalkyl-substituted phenols are already described in general form in U.S. Pat. No. 4,699,971 and U.S. Pat. No. 4,788,276. However, in U.S. Pat. No. 4,699,971 and U.S. Pat. No. 4,788,276 only p-substituted cycloalkyl phenols are explicitly disclosed and cited as being particularly preferred.

Ester-functionalised terminal groups in polycarbonate are likewise already described in general form in CA 13 31 669. However, only p- or p,m-carboxylic acid ester-substituted phenols are described there explicitly and by preference. JP-A 63 21 57 14 describes polycarbonates having reactive terminal groups such as OH and COOH groups.

Chain terminators having the following structures are described in EP-A 09 76 772 specifically for the melt interesterification process:

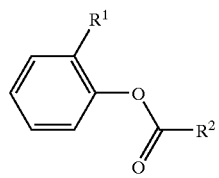

wherein
$R^1$ stands for chlorine, methoxy or ethoxy carbonyl and
$R^2$ stands for an alkyl or alkoxy radical or for an optionally substituted aryl or aryloxy radical.

Also described in EP-A 09 80 861 for the melt interesterification process are salicylic acid derivatives having the following structure:

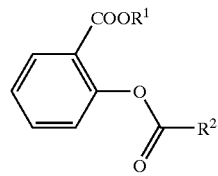

wherein
$R^1$ stands for a methyl or ethyl group and
$R^2$ stands for an alkyl, alkoxy, aryl or aryloxy radical, which is optionally also substituted.

Linear alkyl-substituted and branched alkyl-substituted terminal groups are also known and described e.g. in U.S. Pat. No. 4,269,964. Polycarbonates having alkylamino terminal groups are described in U.S. Pat. No. 3,085,992. Polycarbonates having benzotriazole-substituted terminal groups are known from JP 20 00 06 35 08 A2.

From U.S. Pat. Nos. 3,166,606 and 3,173,891 p-phenyl phenol, for example, is known as a chain terminator for polycarbonates. From U.S. Pat. No. 4,330,663 polyester carbonates are known in which 4-butyl benzoic acid chloride is used as a chain terminator.

WO-A 00/50 488 describes the use of di-tert.-alkyl phenol as a chain terminator.

Polycarbonates that are modified with phenyl propyl phenol, alkyl phenol or naphthol radicals as terminal groups are known from the Japanese laid-open application 57 13 31 49.

Trityl phenol, cumyl phenol, phenoxy phenol and pentadecyl phenol are described in WO-A 01/05 866 as chain terminators for polycarbonate.

From EP-A 10 48 684 and WO-A 99/36 458 polycarbonates are known that are modified with 4-(1,1,3,3-tetramethylbutyl) phenol and other branched alkyl phenols, for example.

According to DE-A 38 03 939 chain terminators having the formula

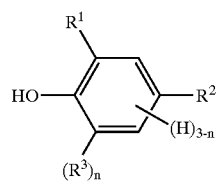

are used, wherein
$R^1$, $R^2$, $R^3$ are the same or different and are $C_2$–$C_{12}$ alkyl or $C_8$–$C_{20}$ aralkyl, at least one of the radicals $R^1$ or $R^2$ being a $C_8$–$C_{20}$ aralkyl radical, and wherein "n" has a value between 0.5 and 1.

Phenols having cycloaliphatic radicals are not described. 2,4- or 2,4,6-substituted phenols are said to be advantageous. Technical mixtures of phenols rather than pure substances are used. The effects of pure substances on the properties of polycarbonate are not described.

EP-A 07 94 209 describes polycarbonates having isooctyl phenol and cumyl phenol terminal groups. JP-A 06 256 499 describes hydroxyaryl-terminated polycarbonates.

Polycarbonates, polyester carbonates and polyesters having the known terminal groups commonly display the disadvantage of a relatively high zero shear-rate viscosity, however, and/or tend towards molecular weight degradation or material discoloration under thermal loading.

Starting from the prior art the object was therefore to provide polycarbonates, polyester carbonates and polyesters having terminal groups, or suitable phenolic compounds to produce said terminal groups, which avoid the disadvantage of a high zero shear-rate viscosity and hence have better processing characteristics. It is also desirable that these terminal groups do not lead to degradation under thermal loading, such as in the extrusion process or injection moulding for example, or in the manufacturing process by the melt interesterification method for example, and thus can also be used e.g. in the melt interesterification method.

DETAILED DESCRIPTION OF THE INVENTION

Surprisingly it has been found that this object is achieved by the use of phenol having substituents in the ortho and/or meta position and no substituent or methyl in the para position as a chain terminator. Preferably the ortho and/or meth positions contain cycloalkyl substituents. These chain terminators or the terminal groups produced from them have a surprisingly positive influence on the zero shear-rate viscosity in the polycarbonate, polyestercarbonate and polyester (herein referred to as polycarbonate) i.e. with a comparable molecular weight distribution the corresponding polycarbonate displays a lower zero shear-rate viscosity and hence better flowability and is therefore more readily processable than polycarbonates having conventional terminal groups. Surprisingly, polycarbonates that are o- and/or m-substituted at the terminal groups derived from the chain terminators, i.e. polycarbonates carrying e.g. o- and/or m-substituted cycloalkyl hydroxybenzoic acid esters and o- and/or m-substituted cycloalkyl phenols as terminal groups display a lower melt viscosity in comparison to corresponding para-substituted compounds. An improvement in melt viscosity is likewise achieved in comparison to conventionally used terminal groups such as e.g. p-tert.-butyl phenol or phenol.

Phenolic chain terminators for polycarbonate that are substituted with cycloalkyl esters have not hitherto been disclosed.

It is true that phenols having cycloalkyl groups are known (U.S. Pat. No. 4,699,971 and U.S. Pat. No. 4,788,276). However, in U.S. Pat. No. 4,699,971 and U.S. Pat. No. 4,788,276 only the p-derivatives are explicitly disclosed as being particularly suitable for the purpose according to the invention. In contrast, however, the o- and/or m-substituted derivatives according to the invention are clearly superior to the p-derivatives of the prior art.

The present invention therefore provides polycarbonates, polyester carbonates and polyesters containing phenolic terminal groups that are o- and/or m-substituted i.e. in particular o- and/or m-cycloalkyl-substituted phenols, which are unsubstituted or methyl-substituted in para position, or are the corresponding o- or m-coupled cycloalkyl-esters, the use of such polycarbonates and special phenolic terminal groups suitable for use in the polycarbonates according to the invention.

The present invention therefore also provides the use of the phenolic compounds according to formula (1) for the production of terminal group-modified polymers.

The phenolic compounds having formula (1) are defined as follows:

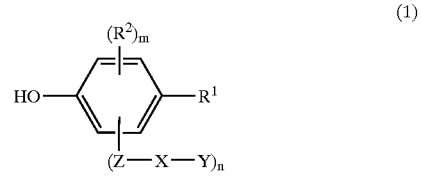

(1)

wherein
$R^1$ is either H or a $CH_3$ radical, preferably H;
$R^2$ stands for H, linear or branched $C_1$–$C_{18}$ alkyl or alkoxy, Cl or Br or an optionally substituted aryl or aralkyl radical, wherein the substitutents are preferably halogenes particularly preferred selected from the group consisting of Fluorine, Chlorine and Bromine; preferably for H or linear or branched $C_1$–$C_{12}$ alkyl; particularly preferably for H or $C_1$–$C_8$ alkyl radical and most particularly preferably for H,
Z stands for an alkylene having 1 to 30 carbon atoms or for a single bond, preferably for an alkylene having 1 to 10 carbon atoms or a single bond and most particularly preferably for a single bond,
X stands for a single bond or a divalent radical such as —O—, —CO—, $CH_2$—, —COO— or —$OCO_2$—,
Y stands for an optionally substituted cycloaliphatic radical or an optionally substituted polycyclic aliphatic radical such as adamantyl or norbornyl radical or an optionally substituted aromatic radical, preferably an optionally substituted cycloaliphatic $C_5$–$C_{12}$ radical or an optionally substituted polycyclic aliphatic radical such as adamantyl or norbornyl radical or an optionally substituted aromatic radical, particularly preferably an optionally substituted cycloaliphatic $C_6$–$C_{12}$ radical or optionally substituted adamantyl or norbornyl radical or an optionally substituted aromatic radical and most particularly preferably an optionally substituted cycloaliphatic $C_6$–$C_{12}$ radical or optionally substituted adamantyl or norbornyl radical, wherein the optional substituents are preferably alkyl or alkoxy groups and halogenes, particularly preferably C1–C15 alkyl or alkoxy groups and F, Cl and Bromine, and
n is 1,2,3 or 4 and m is 0,1,2 or 3, with the proviso that the sum of n plus m is 4, compounds wherein m=3 and n=1 being particularly preferred.

Preferred species within the genus of formula (1) conform to formulae (2), (3) and (4):
Compounds having formula (2)

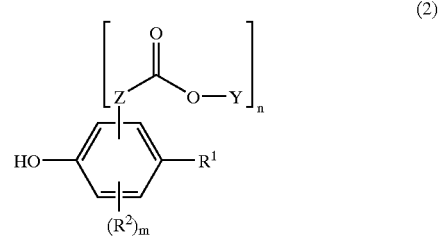

(2)

wherein
Z stands for an alkylene having 1 to 30 carbon atoms or for a single bond, preferably for an alkylene having 1 to 10 carbon atoms or a single bond and most particularly preferably for a single bond,
$R^1$ stands for H or a methyl radical, preferably H, $R^2$ stands for H, linear or branched $C_1$–$C_{18}$ alkyl or alkoxy, Cl or Br or an optionally substituted aryl or aralkyl radical, preferably H or linear or branched $C_1$–$C_{12}$ alkyl, particularly preferably H or $C_1$–$C_8$ alkyl radical and most particularly preferably H, Y stands for an optionally substituted cycloaliphatic $C_5$–$C_{18}$ radical or an optionally substituted polycyclic aliphatic radical such as adamantyl or norbornyl radical or an optionally substituted aromatic radical, preferably an optionally substituted cycloaliphatic $C_5$–$C_{12}$ radical or an optionally substituted polycyclic aliphatic radical such as adamantyl or norbornyl radical or an optionally substituted aromatic radical, particularly preferably an optionally substituted cycloaliphatic $C_6$–$C_{12}$ radical or optionally substituted adamantyl or norbornyl radical or an optionally substituted aromatic radical and most particularly preferably an optionally substituted cycloaliphatic $C_6$–$C_{12}$ radical or optionally substituted adamantyl or norbornyl radical, and n is 1,2,3 or 4 and m is 0,1,2 or 3, with the proviso that the sum of n plus m is 4, compounds wherein m=3 and n=1 being particularly preferred.

Compounds having the formula (3)

$$\left[ \begin{matrix} O \\ \| \\ Z-C-Y \end{matrix} \right]_n \text{HO} \!-\!\!\bigodot\!\!-\!R^1 \quad (R^2)_m \tag{3}$$

wherein

Z stands for an alkylene having 1 to 30 carbon atoms or for a single bond, preferably for an alkylene having 1 to 10 carbon atoms or a single bond and most particularly preferably for a single bond, $R^1$ stands for H or a methyl radical, preferably H, $R^2$ stands for H, linear or branched $C_1$–$C_{18}$ alkyl or alkoxy, Cl or Br or an optionally substituted aryl or aralkyl radical, preferably H or linear or branched $C_1$–$C_{12}$ alkyl, particularly preferably H or $C_1$–$C_8$ alkyl radical and most particularly preferably H, Y stands for an optionally substituted cycloaliphatic $C_5$–$C_{18}$ radical or an optionally substituted polycyclic aliphatic radical such as adamantyl or norbornyl radical or an optionally substituted aromatic radical, preferably an optionally substituted cycloaliphatic $C_5$–$C_{12}$ radical or an optionally substituted polycyclic aliphatic radical such as adamantyl or norbornyl radical or an optionally substituted aromatic radical, particularly preferably an optionally substituted cycloaliphatic $C_6$–$C_{12}$ radical or optionally substituted adamantyl or norbornyl radical or an optionally substituted aromatic radical and most particularly preferably an optionally substituted cycloaliphatic $C_6$–$C_{12}$ radical or optionally substituted adamantyl or norbornyl radical, and n is 1,2,3 or 4 and m is 0,1,2 or 3, with the proviso that the sum of n plus m is 4, compounds wherein m=3 and n=1 being particularly preferred.

Compounds having the formula (4)

$$[Z-Y]_n \ \text{HO}\!-\!\!\bigodot\!\!-\!R^1 \quad (R^2)_m \tag{4}$$

wherein

Z, Y, $R^1$ and $R^2$ having the aforementioned meaning and n is 1,2,3 or 4 and m is 0,1,2 or 3, with the proviso that the sum of n plus m is 4, compounds wherein m=3 and n=1 being particularly preferred.

Most particularly preferred are the phenolic compounds corresponding to formulae (2a), (2b), (3a), (3b), (4a) and (4b):

(2a)

(2b)

(3a)

(3b)

(4a)

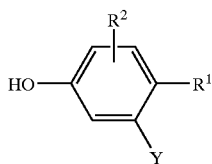

(4b)

the radicals $R^1$, $R^2$ and Y in (2a), (2b), (3a), (3b), (4a) and (4b) having the aforementioned meanings.

Suitable terminal groups derived from the phenolic compounds having formulae (1) to (4) for modifying polycarbonates, polyester carbonates and polyesters are represented by formula (5):

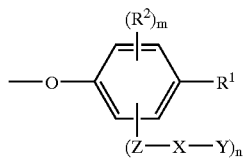

(5)

wherein the radicals and substitution patterns as defined above for formula (1) apply.

Particularly suitable are the terminal groups having formulae (5a) to (5f):

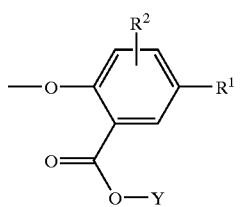

(5a)

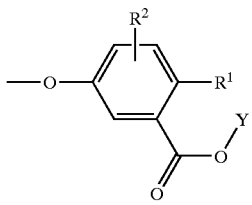

(5b)

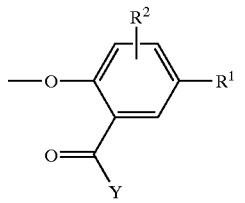

(5c)

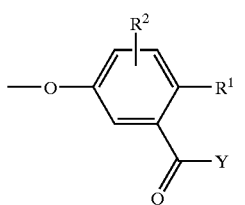

(5d)

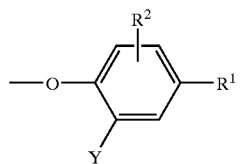

(5e)

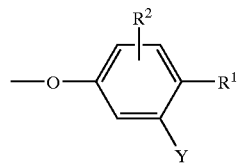

(5f)

wherein the radicals Y, $R^1$ and $R^2$ have the aforementioned meanings.

Most particularly suitable are the terminal groups corresponding to the phenolic compounds having formulae (2a), (2b), (3a), (3b), (4a) and (4b).

Preferred, particularly preferred, most particularly preferred or especially preferred, etc., are compounds carrying the substituents cited under preferred, most particularly preferred or especially preferred, etc.

However, the aforementioned general radical definitions or explanations or those listed in preferential ranges may also be combined in any way with one another, in other words between the individual ranges and preferential ranges. They apply correspondingly for the end products and for the intermediate products or substances.

The present invention therefore also provides thermoplastic polycarbonates, thermoplastic polyester carbonates and thermoplastic polyesters having terminal groups corresponding to the phenolic compounds having formulae (1), (2), (3) and (4).

Examples of phenolic compounds having formula (1) are o-cyclododecyl phenol, o-cyclooctyl phenol, o-cyclohexyl phenol, m-cyclododecyl phenol, m-cyclooctyl phenol, m-cyclohexyl phenol, 3-hydroxybenzophenone, 2-hydroxybenzophenone, 3-hydroxybenzoic acid phenyl ester, 2-hydroxybenzoic acid phenyl ester, 3-hydroxybenzoic acid (4-tert.-butylphenyl) ester, 2-hydroxybenzoic acid (4-tert.-butylphenyl) ester, 3-hydroxybenzoic acid (4-methylphenyl) ester, 2-hydroxybenzoic acid (4-methylphenyl) ester, 3-hydroxybenzoic acid cyclohexyl ester, 2-hydroxybenzoic acid cyclohexyl ester, 3-hydroxybenzoic acid cyclooctyl ester, 2-hydroxybenzoic acid cyclooctyl ester, 3-hydroxybenzoic acid cyclododecyl ester and 2-hydroxybenzoic acid cyclododecyl ester.

Cycloalkyl phenols are generally known in the literature (for example FR-A 15 80 640, U.S. Pat. No. 4,699,971 and U.S. Pat. No. 4,788,276). Hydroxybenzophenones (e.g. EP-A 32 27 5) and hydroxybenzoic acid alkyl esters (DE-A 34 00 342) are also known. Hydroxybenzoic acid cycloalkyl esters are likewise known and described for example in DE-A 34 00 342, JP 60145882 A2 and JP 06001913 A2.

The compounds according to the invention may be produced by known methods.

For example, o-cycloalkyl ester-substituted phenols having formula (5a) may be prepared by reacting salicylic acid esters such as e.g. methyl salicylate with corresponding alcohols with addition of base such as e.g. potassium carbonate or sodium methylate or with addition of interesterification catalysts such as e.g. titanium tetraisopropylate. Corresponding m-substituted compounds having formula (5b) require the use of the corresponding m-hydroxybenzoic acid methyl ester. In these reactions it is recommended that the low-boiling alcohol be removed by distillation during the reaction (see also DE-A 34 00 342).

Compounds having formula (5c) or (5d) may be obtained by Friedel-Crafts acylation such as e.g. by reaction of optionally substituted anisole derivatives with acid chlorides with addition of metal salts such as e.g. $FeCl_3$ or $AlCl_3$. In a second step the phenolic OH group must be released by cleaving the methyl ether. This may be done e.g. with $BBr_3$ or HBr (ether cleavages are described e.g. by A. Kamai, N. L. Gayatri, *Tetrahedron Lett.* 1996, 37, 3359; Friedel-Crafts reactions are described e.g. by H. Heaney, Comprehensive Organic Chemistry; Ed.: B. M. Trost; Pergamon Press Oxford 1991, Vol. 2, p. 753).

Compounds having formula (5e) or (5f) may be produced by reacting phenols with cycloalkenes such as e.g. cyclohexene or cyclooctene at temperatures between 250 and 350° C., optionally with addition of acids such as e.g. sulfuric acid or $BF_3$ (these reactions are described e.g. by W. Jones, *J. Org. Chem.* 1953, 4156 or by Kolka et al., *J. Org. Chem.* 1957, 22, 642).

In addition to the phenolic compounds having formula (1), (2), (3) and (4), other phenols may also additionally be used in quantities of up to 50 mol %, relative to the total amount of chain terminators in each case, to produce the polycarbonates, polyester carbonates and polyesters.

The present invention thus also provides the use of the phenolic compounds having formula (1), optionally in combination with other phenols, as chain terminators in the production of aromatic polycarbonates, aromatic polyester carbonates and aromatic polyesters, wherein the other phenols are used in quantities of up to 50 mol %, preferably up to 25 mol %, relative to the total molar quantity of chain terminators used in each case.

The present invention thus also provides thermoplastic polycarbonates, thermoplastic polyester carbonates and thermoplastic polyesters containing terminal groups derived from the phenolic compounds having formulae (1), (2), (3) and (4), represented for example, but in a non-limiting way, by the polymers having formula (6),

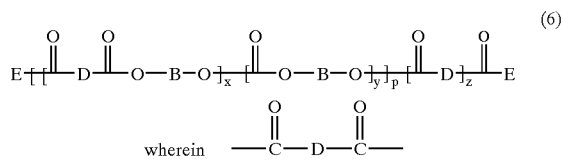

is the radical of an aromatic dicarboxylic acid, —O—B—O is a bisphenolate radical, "p" is a whole number between 25 and 700, "x" and "y" are fractions from the series 0/p, 1/p, 2/p to p/p, wherein x+y=1 and "z"=zero or 1 and at least 50 mol % of the radical E in (6) correspond to the phenolate radicals corresponding to the phenolic compounds having formulae (1), (2), (3) and (4) and a maximum of 50 mol % of the radical E in (6) correspond to a phenolate radical other than that corresponding to the phenolic compounds having formulae (1), (2), (3) or (4).

According to DE-A 2 119 799 polycarbonates are produced using phenolic terminal groups by the interfacial polycondensation process and by the method in the homogeneous phase.

On the production of polycarbonates by the interfacial polycondensation process, reference is made by way of example to H. Schnell, Chemistry and Physics of Polycarbonates, Polymer Reviews, Vol. 9, Interscience Publishers, New York 1964 p. 33 ff. and to Polymer Reviews, Vol. 10, "Condensation Polymers by Interfacial and Solution Methods", Paul W. Morgan, Interscience Publishers, New York 1965, chapter VIII, p. 325.

In addition, the polycarbonates according to the invention may also be produced from diaryl carbonates and diphenols by the known polycarbonate method in the melt, known as the melt interesterification method, as described for example in WO-A 01/05866 and WO-A 01/05867. Interesterification methods (acetate method and phenyl ester method) are also described for example in U.S. Pat. Nos. 3,494,885, 4,386, 186, 4,661,580, 4,680,371 and 4,680,372, in EP-A 26 120, 26 121, 26 684, 28 030, 39 845, 39 845, 91 602, 97 970, 79 075, 14 68 87, 15 61 03, 23 49 13 and 24 03 01, and in DE-A 14 95 626 and 22 32 977. In these methods too, phenolic compounds having o- and/or m-substituents may be used according to the invention as chain terminators.

Diaryl carbonates are such carbonic acid diesters having formula (7)

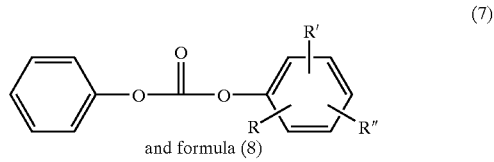

and formula (8)

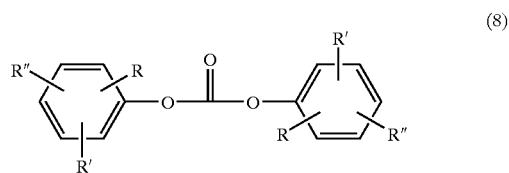

wherein R, R' and R" mutually independently represent H, optionally branched $C_1$–$C_{34}$ alkyl/cycloalkyl, $C_7$–$C_{34}$ alkaryl or $C_6$–$C_{34}$ aryl or $C_6$–$C_{34}$ aryloxy, for example diphenyl carbonate, butylphenyl phenyl carbonate, dibutylphenyl carbonate, isobutylphenyl phenyl carbonate, diisobutylphenyl carbonate, tert.-butylphenyl phenyl carbonate, di-tert.-butylphenyl carbonate, n-pentylphenyl phenyl carbonate, di-(n-pentylphenyl) carbonate, n-hexylphenyl phenyl carbonate, di-(n-hexylphenyl) carbonate, cyclohexylphenyl phenyl carbonate, di-cyclohexylphenyl carbonate, phenylphenol phenyl carbonate, diphenylphenol carbonate, isooctylphenyl phenyl carbonate, diisooctylphenyl carbonate, n-nonylphenyl phenyl carbonate, di-(n-nonylphenyl) carbonate, cumylphenyl phenyl carbonate, dicumylphenyl carbonate, naphthylphenyl phenyl carbonate, dinaphthylphenyl carbonate, di-tert.-butylphenyl phenyl carbonate, di-(di-tert.-butylphenyl) carbonate, dicumylphenyl phenyl carbonate, di-(dicumylphenyl) carbonate, 4-phenoxyphenyl phenyl carbonate, di-(4-phenoxyphenyl) carbonate, 3-pentadecylphenyl phenyl carbonate, di-(3-pentadecylphenyl) carbonate, tritylphenyl phenyl carbonate, ditritylphenyl carbonate, preferably diphenyl carbonate, tert.-butylphenyl phenyl carbonate, di-tert.-butylphenyl carbonate, phenylphenol phenyl carbonate, diphenylphenol carbonate, cumylphenyl phenyl carbonate, dicumylphenyl carbonate, particularly preferably diphenyl carbonate.

Diphenols for the polycarbonates according to the invention include hydroquinone, resorcinol, dihydroxy biphenyls, bis-(hydroxyphenyl) alkanes, bis-(hydroxyphenyl) cycloalkanes, bis-(hydroxyphenyl) sulfides, bis-(hydroxyphenyl) ethers, bis-(hydroxyphenyl) ketones, bis-(hydroxyphenyl) sulfones, bis-(hydroxyphenyl) sulfoxides, α,α'-bis-(hydroxyphenyl) diisopropyl benzenes, as well as ring-alkylated and ring-halogenated compounds thereof, and also α,ω-bis-(hydroxyphenyl) polysiloxanes.

Preferred diphenols include 4,4'-dihydroxybiphenyl (DOD), 2,2-bis-(4-hydroxyphenyl) propane (bisphenol A), 1,1-bis-(4-hydroxyphenyl)-3,3,5-trimethyl cyclohexane (bisphenol TMC), 1,1-bis-(4-hydroxyphenyl) cyclohexane, 2,4-bis-(4-hydroxyphenyl)-2-methyl butane, 1,1-bis-(4-hydroxyphenyl)-1-phenyl ethane, 1,1-bis-(4-hydroxyphenyl)-p-diisopropyl benzene, 1,3-bis-[2-(4-hydroxyphenyl)-2-propyl] benzene (bisphenol M), 2,2-bis-(3-methyl-4-hydroxyphenyl) propane, 2,2-bis-(3-chloro-4-hydroxyphenyl) propane, bis-(3,5-dimethyl-4-hydroxyphenyl) methane, 2,2-bis-(3,5-dimethyl-4-hydroxyphenyl) propane, bis-(3,5-dimethyl-4-hydroxyphenyl) sulfone, 2,4-bis-(3,5-dimethyl-4-hydroxyphenyl)-2-methyl butane, 2,2-bis-(3,5-dichloro-4-hydroxyphenyl) propane and 2,2-bis-(3,5-dibromo-4-hydroxyphenyl) propane.

Particularly preferred diphenols are 2,2-bis-(4-hydroxyphenyl) propane (bisphenol A), 1,3-bis-[2-(4-hydroxyphenyl)-2-propyl] benzene (bisphenol M), 2,2-bis-(3,5-dimethyl-4-hydroxyphenyl) propane, 1,1-bis-(4-hydroxyphenyl)-1-phenyl ethane, 2,2-bis-(3,5-dichloro-4-hydroxyphenyl) propane, 2,2-bis-(3,5-dibromo-4-hydroxyphenyl) propane, 1,1-bis-(4-hydroxyphenyl) cyclohexane and 1,1-bis-(4-hydroxyphenyl)-3,3,5-trimethyl cyclohexane (bisphenol TMC).

Most particularly preferred are 2,2-bis-(4-hydroxyphenyl) propane (bisphenol A), 1,3-bis-[2-(4-hydroxyphenyl)-2-propyl] benzene (bisphenol M) and 1,1-bis-(4-hydroxyphenyl)-3,3,5-trimethyl cyclohexane (bisphenol TMC).

The diphenols may be used both alone and in combination with one another; they include both homopolycarbonates and copolycarbonates. The diphenols are known from the literature or may be produced by methods known from the literature (see e.g. H. J. Buysch et al., Ullmann's Encyclopedia of Industrial Chemistry, VCH, New York 1991, 5$^{th}$ Ed., Vol. 19, p. 348).

Small quantities, preferably quantities of between 0.05 and 2.0 mol %, relative to the moles of diphenols used, of trifunctional or polyfunctional compounds, in particular those having three or more phenolic hydroxyl groups as so-called branching agents, may additionally be used. This naturally leads to deviations from the idealized formula (6), which is cited by way of example only, since branching structures are then formed rather than the cited structures D and B.

Some of the compounds having three or more phenolic hydroxyl groups that may be used are for example phloroglucinol, 4,6-dimethyl-2,4,6-tri-(4-hydroxyphenyl)-hept-2-ene, 4,6-dimethyl-2,4,6-tri-(4-hydroxyphenyl) heptane, 1,3,5-tri-(4-hydroxyphenyl) benzene, 1,1,1-tri-(4-hydroxyphenyl) ethane, tri-(4-hydroxyphenyl) phenyl methane, 2,2-bis-[4,4-bis-(4-hydroxyphenyl) cyclohexyl] propane, 2,4-bis-(4-hydroxyphenyl isopropyl) phenol, 2,6-bis-(2-hydroxy-5'-methyl benzyl)-4-methyl phenol, 2-(4-hydroxyphenyl)-2-(3,4-dihydroxyphenyl) propane, hexa-[4-(4-hydroxyphenyl isopropyl) phenyl] orthoterephthalic acid ester, tetra-[4-(4-hydroxyphenyl isopropyl) phenoxy] methane, tetra-(4-hydroxyphenyl) methane and 1,4-bis-(4', 4"-dihydroxytriphenyl) methyl benzene.

Other possible branching agents are 2,4-dihydroxybenzoic acid, trimesic acid, cyanuric chloride and 3,3-bis-(3-methyl-4-hydroxyphenyl)-2-oxo-2,3-dihydroindole.

The 0.05 to 2 mol %, relative to diphenols used, of branching agents that may optionally additionally be used may either be introduced into the aqueous alkaline phase together with the diphenols themselves and the molecular weight regulators according to the invention or added prior to phosgenation, dissolved in an organic solvent.

The aromatic polycarbonates according to the present invention have weight-average molecular weights $M_w$ (determined by gel permeation chromatography and calibration with polystyrene standard) of between 5,000 and 200,000, preferably between 10,000 and 80,000 and particularly preferably between 15,000 and 40,000.

The relative solution viscosities are accordingly 1.10 to 1.60, measured in methylene chloride (0.5 g polycarbonate in 100 ml methylene chloride at 23° C.).

Polyester carbonates according to the invention are those made up of at least one diphenol, at least one aromatic dicarboxylic acid and carbonic acid.

Suitable aromatic dicarboxylic acids are for example orthophthalic acid, terephthalic acid, isophthalic acid, tert.-butyl isophthalic acid, 3,3'-diphenyl dicarboxylic acid, 4,4'-diphenyl ether dicarboxylic acid, 4,4'-diphenyl sulfone dicarboxylic acid, 3,4'-benzophenone dicarboxylic acid, 2,2-bis(4-carboxyphenyl) propane, trimethyl-3-phenylindane-4,5-dicarboxylic acid.

Of the aromatic dicarboxylic acids, terephthalic acid and/or isophthalic acid are particularly preferably used.

Suitable diphenols are those specified above for polycarbonate production. The carbonic acid may be incorporated into the polyester carbonates either via phosgene or via diphenyl carbonate, depending on which production method is chosen, in other words depending on whether interfacial polycondensation or melt interesterification is used for polyester carbonate production.

The same applies to the aromatic dicarboxylic acids; they are either used as aromatic dicarboxylic acid dichlorides in the interfacial polycondensation process or as dicarboxylic acid diesters in the melt interesterification process.

The polyester carbonates according to the invention are produced by known production methods, in other words as already mentioned by the interfacial polycondensation process or by the melt interesterification process, for example.

The polyester carbonates according to the invention may be linear or branched by known means. The aromatic polyester carbonates according to the present invention have weight-average molecular weights $M_w$ (determined by gel permeation chromatography with polystyrene calibration) preferably between 10,000 and 250,000.

The molar ratio of carbonate units to aromatic dicarboxylate units in the polyester carbonates according to the invention is preferably 95:5 to 5:95, particularly preferably 90:10 to 10:90, especially preferably 80:20 to 20:80 and most particularly preferably 60:40 to 40:60.

In the case of the polyesters (6) according to the invention "z" may be 0 or 1.

Aromatic polyesters according to the invention are those consisting of at least one diphenol and at least one aromatic dicarboxylic acid.

Suitable diphenols and dicarboxylic acids are those cited above for polyester carbonate production.

The aromatic polyesters according to the invention are produced by known production methods (see e.g. Kunststoff-Handbuch, Vol. VIII, p. 695 ff, Carl-Hanser-Verlag, Munich, 1973).

The aromatic polyesters according to the invention may be linear or branched by known means.

The aromatic polyesters according to the invention have weight-average molecular weights $M_w$ (determined by the light scattering method) preferably between 25,000 and 70,000; this corresponds to degrees of polymerisation "p" in formula (6) of around 80 to 270, wherein "x"=1, "y"=0 and z=1.

The quantity of monophenols according to the invention having formula (1), (2) or (3) to be used in producing the polycarbonates, polyester carbonates or polyesters according to the invention is between 0.5 mol % and 8 mol %, preferably between 2 mol % and 6 mol %, relative to the diphenols used in each case.

The conventional monophenols such as for example phenol, 4-alkyl phenols and 4-cumyl phenol are suitable as additional chain terminators.

The present invention therefore also provides a process for the production of the polycarbonates, polyester carbonates or polyesters according to the invention from diphenols, monophenols, carbonic acid derivatives and/or dicarboxylic acid derivatives according to process conditions known per se, characterized in that monophenols having formula (1), (2), (3) or (4) are used as chain terminators in quantities of 0.5 mol % to 8 mol %, preferably 2 mol % to 6 mol %, relative in each case to moles of diphenols, wherein up to 50 mol % thereof, preferably up to 25 mol %, relative in each case to the total quantity of chain terminators, may be replaced by other monophenols.

If the interfacial polycondensation process is used, the chain terminators having formula (1), (2), (3) or (4) may be added in solution before, during or after phosgenation. The suitable solvents for dissolving the chain terminators having formula (1), (2), (3) or (4) are for example methylene chloride, chlorobenzene or acetonitrile as well as mixtures of these solvents.

If the melt interesterification process is used, the chain terminators having formula (1), (2), (3) or (4) may be added according to the invention at any point during the reaction; the addition may be divided into several portions.

The invention also provides the polycarbonates, polyester carbonates and polyesters obtainable by the process according to the invention.

Diphenols for producing the polycarbonates, polyester carbonates and polyesters according to the invention may also be polymers or condensates having phenolic terminal groups, such that polycarbonates or polyester carbonates or polyesters having block structures are also included according to the invention.

The polycarbonates, polyester carbonates and polyesters according to the invention may be worked up by known means and processed to produce any type of molded parts, by extrusion or injection moulding for example.

Other aromatic polycarbonates and/or other aromatic polyester carbonates and/or other aromatic polyesters may also be added to the polycarbonates, polyester carbonates and polyesters according to the invention by known means.

Conventional additives for these thermoplastics, such as fillers, UV stabilisers, heat stabilisers, antistatic agents and pigments may also be added to the polycarbonates, polyester carbonates and polyesters according to the invention in the conventional quantities; the demolding behaviour, flow properties and/or flame resistance may optionally also be improved by the addition of external mold release agents, flow control agents and/or flame retardants (e.g. alkyl and aryl phosphites, phosphates, phosphanes, low-molecular carboxylic acid esters, halo compounds, salts, chalk, silica flour, glass and carbon fibres, pigments and combinations thereof. Such compounds are described e.g. in WO 99/55772, p. 15–25 and in "Plastics Additives", R. Gächter and H. Müller, Hanser Publishers 1983).

Once processed into molded parts/extrudates of any type, the polycarbonates, polyester carbonates and polyesters according to the invention, optionally blended with other thermoplastics and/or conventional additives, may be used wherever known polycarbonates, polyester carbonates and polyesters are already used. Their range of properties also makes them particularly suitable as substrate materials for optical data storage media such as e.g. CDs, CD-Rs, DVDs or DVD-Rs, but they may also be used for example as films in the electrical sector, as moldings in vehicle construction and as sheets for covers in the safety sector. Other possible applications for the polycarbonates according to the invention are:

1. Safety glass, which is known to be needed in many areas of buildings, vehicles and aircraft, and as visors for helmets.
2. Production of films, particularly films for skis.
3. Production of blow moldings (see e.g. U.S. Pat. No. 2,964,794), for example 1 to 5 gallon water bottles.
4. Production of translucent sheets, in particular twin-wall sheets, for example for covering buildings such as stations, greenhouses and lighting installations.
5. Production of optical data storage media.
6. For producing traffic light housings or road signs.
7. For producing foams (see e.g. DE-B 1 031 507).
8. For producing threads and wires (see e.g. DE-B 1 137 167 and DE-A 1 785 137).
9. As translucent plastics containing glass fibres for lighting applications (see e.g. DE-A 1 554 020).
10. As translucent plastics containing barium sulfate, titanium dioxide and/or zirconium oxide or organic polymeric acrylate rubbers (EP-A 634 445, EP-A 269324) for producing translucent and light-scattering molded parts.
11. For producing precision injection moldings, such as e.g. lens holders. Polycarbonates having a content of glass fibres and optionally additionally containing around 1–10 wt. % $MoS_2$, relative to the total weight, are used for this purpose.
12. For producing optical device components, in particular lenses for photographic and film cameras (see e.g. DE-A 2 701 173).
13. As light carriers, in particular as optical cables (see e.g. EP-A 0 089 801).
14. As electrical insulating materials for electrical cables and for connector shells and plug-in connectors.
15. Manufacture of mobile telephone housings with improved resistance to perfume, aftershave and perspiration.
16. Network interface devices.
17. As supports for organic photoconductors.
18. For manufacturing lamps, e.g. headlamps, diffusers or internal lenses.
19. For medical applications, e.g. oxygenators, dialysis machines.
20. For food applications, such as e.g. bottles, crockery and chocolate moulds.
21. For applications in the automotive sector, e.g. in areas coming into contact with fuels and lubricants, such as e.g. bumpers, optionally in the form of suitable blends with ABS or suitable rubbers.
22. For sports articles, such as e.g. slalom poles or ski boot clips.
23. For domestic items such as e.g. kitchen sinks and letterboxes.
24. For housings, such as e.g. electrical distribution cabinets.
25. Housings for electric toothbrushes and hairdryer housings.

26. Transparent washing machine portholes with improved resistance to detergent solution.
27. Protective goggles, optical correction spectacles.
28. Lamp covers for kitchen appliances with improved resistance to kitchen fumes, particularly oil fumes.
29. Packaging films for drug products.
30. Chip boxes and chip carriers.
31. For other applications, such as e.g. stable doors or animal cages.

This application also provides the molded parts and extrudates produced from the polymers according to the invention.

EXAMPLES

Example 1
Preparation of 4-hydroxybenzoic Acid Cyclooctyl Ester 22.82 g (0.15 mol) p-hydroxybenzoic acid methyl ester, 38.47 g (0.30 mol) cyclooctanol and 26 mg (0.1 mmol) tetraisopropyl orthotitanate are placed under argon in a round-bottom flask with distillation bridge. The mixture is stirred and heated to 180° C. within 45 minutes. The pressure is reduced to 800 mbar and over the further course of distillation to 650 mbar. After a further 15 minutes the pressure is increased to 900 mbar and the reaction mixture stirred for a further 2 hours, during which time methanol continues to be removed by distillation. A further 9.62 g (0.075 mol) cyclooctanol and 2 drops of tetraisopropyl orthotitanate are added to the reaction solution and stirred for a further 4 hours at 180° C. It is allowed to cool and the residue is dissolved in 100 ml ethyl acetate and washed repeatedly with distilled water. The organic phase is concentrated to small volume. The crude product is purified by column chromatography (silica gel 60, 0040–0.063 mm, Merck) with an n-hexane/acetone mixture (3:1). The product obtained is freed from adhering cyclooctanol under high vacuum. The white crystalline residue is recrystallised in acetone. 4.70 g (12%) of colourless crystals are obtained.

Melting point: 109–111° C.

$^1$H-NMR (400 MHz, CDCl$_3$) δ=7.94 (d, 2H), 6.87 (d, 2H), 6.15 (s, 1H), 5.21–5.13 (m, 1H), 2.00–1.72 (m, 6 H), 1.70–1.45 (m, 8H).

Example 2
Preparation of 4-hydroxybenzoic Acid Cyclododecyl Ester:

22.82 g (0.15 mol) p-hydroxybenzoic acid methyl ester, 55.30 g (0.30 mol) cyclododecanol and 28 mg (0.1 mmol) tetraisopropyl orthotitanate are placed under argon in a round-bottom flask with distillation bridge. The mixture is stirred and heated to 160° C. within one hour. On reaching this temperature the pressure is reduced to 900 mbar and during the further course of the reaction to 800 mbar, during which time methanol is removed by distillation. Stirring is continued for 5 hours at this temperature. A further 0.05 ml tetraisopropyl orthotitanate are added and the reaction mixture is stirred for a further 20 hours at 170° C. under normal pressure. The residue undergoes column chromatography (silica gel 60, 0040–0.063 mm, Merck). An n-hexane/acetone mixture (5:1) is used as eluent. The product obtained in this way is freed from adhering cyclododecanol under high vacuum at 140° C. The residue is recrystallised in acetone. 5.9 g (13%) in the form of colourless crystals are obtained:

$^1$H-NMR (400 MHz, CDCl$_3$) δ=7.94 (d, 2H), 6.86 (d, 2H), 6.08 (s, 1H), 5.27–5.19 (m, 1H), 1.89–1.75 (m, 2H), 1.68–1.55 (m, 2H), 1.53–1.25 (m, 18H).

Example 3
Preparation of 3-hydroxybenzoic Acid Cyclooctyl Ester:

15.22 g (0.10 mol) m-hydroxybenzoic acid methyl ester, 25.64 g (0.20 mol) cyclooctanol and 15 mg (0.05 mmol) tetraisopropyl orthotitanate are placed under argon in a round-bottom flask with distillation bridge. The mixture is stirred and heated to 170–180° C. Stirring is continued for 3.5 hours and a further 12.82 g (0.10 mol) cyclooctanol are added. After a further 5 hours at 170–180° C. a further 12.8 g cyclooctanol and 15 mg tetraisopropyl orthotitanate are added to the solution and stirring is continued for a further 7 hours at temperatures between 190 and 210° C.

It is allowed to cool and approx. 500 ml distilled water are added to the reaction solution. Extraction is performed repeatedly with diethyl ether. The combined organic phases are washed with saturated NaCl solution. After drying over magnesium sulfate the solvent is removed in vacuo. The crude product is chromatographed with a mixture of n-hexane and ethyl acetate (5:1) on silica gel (silica gel 60, 0040–0.063 mm, Merck). The product is heated under high vacuum to remove residual cyclooctanol. 16.03 g (65%) in the form of a brown viscous oil are obtained.

$^1$H-NMR (400 MHz, CDCl$_3$) δ=7.68–7.65 (m, 1H), 7.61–7.55 (m, 1H), 7.32–7.23 (m, 1H), 7.12–7.05 (m, 1H), 6.96 (s, 1H), 5.24–5.12 (m, 1H), 1.77–1.45 (m, 14H).

Example 4
Preparation of 3-hydroxybenzoic Acid Cyclododecyl Ester:

15.22 g (0.10 mol) m-hydroxybenzoic acid methyl ester, 38.86 g (0.20 mol) cyclododecanol and 19 mg (0.07 mmol) tetraisopropyl orthotitanate are placed under argon in a round-bottom flask with distillation bridge. The reaction mixture was heated to 175° C. and the pressure reduced to 800 mbar. The pressure was continually reduced to 500 mbar within 2 hours. After a further 4 hours a further 3 drops of tetraisopropyl orthotitanate are added. The pressure is increased to 800 mbar. Stirring was continued for a further 24 hours at 170–200° C. It is allowed to cool and the residue is purified by column chromatography on silica gel (silica gel 60, 0040–0.063 mm, Merck) with an n-hexane/acetone mixture (5:1). The product obtained is freed from adhering cyclododecanol in high vacuum and chromatographed again with dichloromethane on silica gel (silica gel 60, 0040–0.063 mm, Merck). 5.2 g (17%) of a brown-yellow solid are obtained.

$^1$H-NMR (400 MHz, CDCl$_3$) δ=7.61–7.52 (m, 2H), 7.35–7.22 (m, 1H), 7.08–7.00 (m, 1H), 5.56 (s, 1H), 5.32–5.28 (m, 1H), 1.90–1.75 (m, 2H), 1.74–1.56 (m, 2H), 1.54–1.22 (m, 18H).

Example 5
Preparation of Polycarbonate Having a Terminal Group According to the Invention:

17.12 g (0.075 mol) 2,2-bis-(4-hydroxyphenyl) propane and 6.60 g NaOH (220 mol %, relative to the bisphenol component) are dissolved in 273 ml water in a flask under a nitrogen atmosphere. 1.12 g (6 mol % relative to the bisphenol component) 3-hydroxybenzoic acid cyclooctyl ester (see Example 3) dissolved in 273 ml dichloromethane are added to this mixture. It is stirred for 5 minutes. 14.73 g (200 mol %, relative to the bisphenol component) of phosgene are introduced at room temperature (25° C.) and with vigorous stirring. During this process the pH is kept in the range of pH=12.5–13.5 by making up with 40% NaOH solution. On completion of the introduction the apparatus is rinsed with nitrogen for 5 minutes. 0.085 g (1 mol %) N-ethyl piperidine dissolved in 10 ml dichloromethane are added to the reaction mixture. Stirring is continued for a further 45 minutes. It is then diluted with dichloromethane and the organic phase separated off. After extracting the organic phase with the same volume of 10% hydrochloric acid the organic phase is separated off and washed a further 5 times with water until it is free from electrolytes. The polymer dissolved in the organic phase is precipitated in methanol and dried in vacuo.

Yield: 18.90 g (before precipitation)
$M_n$=10005 g/mol
$M_w$=19163 g/mol
D=1.92
$T_g$=147° C.

Example 6
Preparation of Polycarbonate Having a Terminal Group According to the Invention:

The performance of the experiment corresponds to the instructions for Example 5. The difference is that—in place of 3-hydroxybenzoic acid cyclooctyl ester—6 mol % (relative to the bisphenol component) 3-hydroxybenzoic acid cyclododecyl ester (see Example 4) is used as the chain terminator.
$M_n$=8384
$M_w$=20423
D=2.44
$T_g$=142° C.

Example 7
Comparative Example

The performance of the experiment corresponds to the instructions for Example 5. The difference is that the chain terminator is dissolved in the two-phase system before phosgenation. 6 mol % (relative to the bisphenol component) 4-tert.-butyl phenol is used as the chain terminator in place of 3-hydroxybenzoic acid cyclooctyl ester.
$M_n$=10238
$M_w$=19431
D=1.90
$T_g$=148° C.

Example 8
Comparative Example

The performance of the experiment corresponds to the instructions for Example 5. The difference is that 5 mol % (relative to the bisphenol component) 4-hydroxy-benzoic acid cyclooctyl ester is used as the chain terminator in place of 3-hydroxybenzoic acid cyclooctyl ester.
$M_n$=11679
$M_w$=22793
D=1.95
$T_g$=149° C.

Terminal Groups According to the Invention:

| Ex. no. | Terminal group used | Zero shear-rate viscosity (Pa · s) (at 270° C.) | Molecular weight (g/mol) | Glass transition temperature (° C.) |
|---|---|---|---|---|
| 5 | [structure: 3-hydroxybenzoic acid cyclooctyl ester] | 140 | $M_w$ = 19163 $M_n$ = 10005 | 147 |
| 6 | [structure: 3-hydroxybenzoic acid cyclododecyl ester] | 75 | $M_w$ = 20423 $M_n$ = 8384 | 142 |

Comparative Examples

| Ex. no. | Terminal group used | Zero shear-rate viscosity (Pa · s) (at 270° C.) | Molecular weight (g/mol) | Glass transition temperature (° C.) |
|---|---|---|---|---|
| 7 | [structure: 4-tert-butylphenol] | 350 | $M_w$ = 19431 $M_n$ = 10238 | 148 |

-continued

| Ex. no. | Terminal group used | Zero shear-rate viscosity (Pa · s) (at 270° C.) | Molecular weight (g/mol) | Glass transition temperature (° C.) |
|---|---|---|---|---|
| 8 | 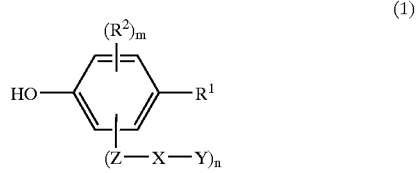 | 510 | $M_w = 22793$<br>$M_n = 11679$ | 149 |

It may be seen from the tables above that compared with polycarbonates having p-substituted phenols, such as e.g. having conventional terminal groups such as tert.-butyl phenol, the polycarbonates according to the invention surprisingly display a reduced zero shear-rate viscosity with a virtually identical molecular weight.

Example 9
Preparation of 2-cyclododecyl Phenole:

83.0 g (0.499 mol) cyclododecene (Aldrich), 470.7 g (5.00 mol) freshly distilled phenole and 276 g of ion-exchanging resin Lewatit S100, acidic (Bayer AG) are placed in a round-bottom flask. The reaction mixture was heated to 73–74° C. Stirring was continued for 24 hours at 74° C. It is allowed to cool to room temperature followed by filtration in order to separate the crude product from the ion-exchanging resin. The product mixture is distilled under reduced pressure to remove phenol. The residue is purified by column chromatography on silica gel with toluene. The product obtained is freed from adhering toluene in high vacuum. 91.2 g (70%) of a white solid are obtained.

$^1$H-NMR (400 MHz, CDCl$_3$) δ=9.10 (s, 1H), 7.1–7.0 (m, 1H), 7.0–6.85 (m, 1H), 6.85–6.65 (m, 2H), 3.30–3.15 (m, 1H), 1.85–1.05 (m, 22H).

Example 10
Preparation of Polycarbonate Having a Terminal Group According to the Invention:

22.83 g (0.1 mol) 2,2-bis-(4-hydroxyphenyl) propane and 8.80 g NaOH (220 mol %, relative to the bisphenol component) are dissolved in 173 ml water in a flask under a nitrogen atmosphere. 2.865 g (11 mol % relative to the bisphenol component) 2-cyclododecyl phenole (see Example 9) dissolved in 173 ml dichloromethane are added to this mixture. It is stirred for 5 minutes. 20.62 g (200 mol %, relative to the bisphenol component) of phosgene are introduced at room temperature (25° C.) and with vigorous stirring. During this process the pH is kept in the range of pH=12.5–13.5 by making up with 40% NaOH solution. On completion of the introduction the apparatus is rinsed with nitrogen for 5 minutes. 0.11 g (1 mol %) N-ethyl piperidine dissolved in 10 ml dichloromethane are added to the reaction mixture. Stirring is continued for a further 45 minutes. It is then diluted with dichloromethane and the organic phase separated off. After extracting the organic phase with the same volume of 10% hydrochloric acid the organic phase is separated off and washed a further 5 times with water until it is free from electrolytes. The polymer dissolved in the organic phase is precipitated in methanol and dried in vacuo.

Yield: 23.67 g (before precipitation)
$M_n$=10205 g/mol
$M_w$=18635 g/mol
D=1.83
$T_g$=133° C.

| Ex. no. | Terminal group used | Zero shear-rate viscosity (Pa · s) (at 270° C.) | Molecular weight (g/mol) | Glass transition temperature (° C.) |
|---|---|---|---|---|
| 10 | 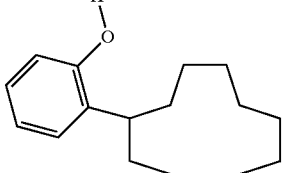 | 240 | $M_w = 18635$<br>$M_n = 10205$ | 133 |

Although the invention has been described in detail in the foregoing for the purpose of illustration, it is to be understood that such detail is solely for that purpose and that variations may be made therein by those skilled in the art without departing from the spirit and scope of the invention except as it may be limited by the claims.

What is claimed is:

1. A process of using of at least one member selected from a first group consisting of compounds conforming to formula (1)

$$\text{(1)}$$

wherein
R$^1$ is either H or a CH$_3$ radical;
R$^2$ denotes a member selected from the group consisting of H, linear C$_1$–C$_{18}$ alkyl, branched C$_1$–C$_{18}$ alkyl, linear $C_1$–$C_{18}$ alkoxy, branched $C_1$–$C_{18}$ alkoxy, Cl, Br, aryl radical and aralkyl radical, Z denotes an alkylene having 1 to 30 carbon atoms or a single bond, X denotes a single bond or a divalent radical, Y denotes a member selected from the group consisting of a cycloaliphatic radical, polycyclic aliphatic radical and an aromatic radical, and n is 1, 2, 3 or 4 and m is 0, 1, 2 or 3, with the proviso that the sum of n plus m is 4, comprising adding said phenol as a chain terminator to the reaction that entails at least one diphenol in the preparation of a member selected from a second group consisting polycarbonate, polyester carbonate and polyester.

2. The polycarbonate prepared by the process of claim 1.

3. The polyester carbonate prepared by the process of claim 1.

4. The polyester prepared by the process of claim 1.

5. A molded article comprising the polycarbonate of claim 2.

6. A molded article comprising the polyester carbonate of claim 3.

7. A molded article comprising the polyester of claim 4.

8. The process of claim 1 wherein member of the first group is present in an amount of 0.5 to 8 mol %, relative to the total moles of diphenol.

9. The process of claim 8 wherein the amount is 2 to 6 mol %.

10. The compound according to formula (1) according to claim 1.

11. The compound of claim 10 wherein at least one of said aryl radical and aralkyl radical are substituted.

12. The compound of claim 10 wherein X denotes a divalent radical selected from the group consisting of —O—, —CO—, CH$_2$—, —COO— and —OCO$_2$—.

13. The compound of claim 10 wherein Y is substituted.

14. The process of claim 1 wherein the o- and/or m-substituent is cycloalkyl.

15. The process of claim 1 wherein the member of the first group conform to formula (1)

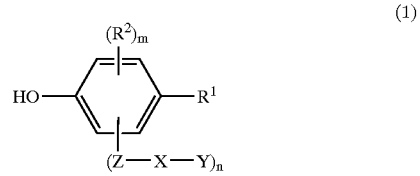

wherein

R$^1$ is either H or a CH$_3$ radical;

R$^2$ denotes a member selected from the group consisting of H, linear $C_1$–$C_{18}$ alkyl, branched $C_1$–$C_{18}$ alkyl, linear $C_1$–$C_{18}$ alkoxy, branched $C_1$–$C_{18}$ alkoxy, Cl, Br, aryl radical and aralkyl radical, Z denotes an alkylene having 1 to 30 carbon atoms or a single bond, X denotes a single bond or a divalent radical, Y denotes a member selected from the group consisting of a cycloaliphatic radical, polycyclic aliphatic radical and an aromatic radical, and n is 1, 2, 3 or 4 and m is 0, 1, 2 or 3, with the proviso that the sum of n plus m is 4.

16. The process of claim 15 wherein member of the second group is polycarbonate.

17. The process of claim 15 wherein member of the second group is polyester carbonate.

18. The process of claim 15 wherein member of the second group is polyester.

19. The polycarbonate prepared by the process of claim 16.

20. The polyester carbonate prepared by the process of claim 17.

21. The polyester prepared by the process of claim 18.

* * * * *